US012629245B2

(12) United States Patent
Tucker et al.

(10) Patent No.: US 12,629,245 B2
(45) Date of Patent: May 19, 2026

(54) METHODS AND SYSTEMS FOR PREDICTING THE POST-OPERATIVE EFFECTIVE LENS POSITION IN CATARACT SURGERY

(71) Applicant: The Regents of the University of California, Oakland, CA (US)

(72) Inventors: James Tucker, Roseville, CA (US); Matthew Wade, Placentia, CA (US); Sumit Garg, Tustin, CA (US); Caleb Shumway, New York, NY (US)

(73) Assignee: The Regents of the University of California, Oakland, CA (US)

( * ) Notice: Subject to any disclaimer, the term of this patent is extended or adjusted under 35 U.S.C. 154(b) by 1009 days.

(21) Appl. No.: 17/841,623

(22) Filed: Jun. 15, 2022

(65) Prior Publication Data

US 2022/0401211 A1 Dec. 22, 2022

Related U.S. Application Data

(60) Provisional application No. 63/212,559, filed on Jun. 18, 2021.

(51) Int. Cl.
*A61F 2/16* (2006.01)
*A61B 3/10* (2006.01)
(52) U.S. Cl.
CPC .............. *A61F 2/16* (2013.01); *A61B 3/1005* (2013.01); *A61F 2240/002* (2013.01)

(58) Field of Classification Search
CPC .... A61F 2/16; A61F 2/1627; A61F 2002/482; A61F 2240/002
See application file for complete search history.

(56) References Cited

U.S. PATENT DOCUMENTS 9,554,697 B2 * 1/2017 Padrick .................. G02C 7/022
2009/0281552 A1 * 11/2009 Hiramatsu ............. A61B 3/107
606/107

OTHER PUBLICATIONS

Olsen T, Olesen H, Thim K, Corydon L, "Prediction of pseudophakic anterior chamber depth with the newer IOL calculation formulas." J Cataract Refract Surg. 1992; 18(3):280-285.
Olsen T, Corydon L, Gimbel H., "Intraocular lens power calculation with an improved anterior chamber depth prediction algorithm." J Cataract Refract Surg. 1995; 21(3):313-319.
Olsen T., "Prediction of the effective postoperative (intraocular lens) anterior chamber depth." J Cataract Refract Surg. 2006; 32(3):419-424.
Holladay JT, Prager TC, Chandler TY, Musgrove KH, Lewis JW, Ruiz RS., "A three-part system for refining intraocular lens power calculations." J Cataract Refract Surg. Jan. 1988; 14(1):17-24.
Hoffer KJ, "The Hoffer Q formula: A comparison of theoretic and regression formulas." J Cataract Refract Surg. 1993; 19(6):700-712.

(Continued)

*Primary Examiner* — Vi X Nguyen
(74) *Attorney, Agent, or Firm* — Robert D. Buyan; Stout, Uxa & Buyan, LLP

(57) ABSTRACT

Methods and systems for predicting the post-operative effective lens position (ELP) of a prosthetic intraocular lens (IOL) in cataract surgery using novel pre-operative measurement(s) of the natural lens curvatures.

11 Claims, 6 Drawing Sheets

(56)         References Cited

OTHER PUBLICATIONS

Retzlaff JA, Sanders DR, Kraff MC., "Development of the SRK/T intraocular lens implant power calculation formula." J Cataract Refract Surg. 1990; 16(3):333-340.

Tamaoki A., et al., "Prediction of Effective Lens Position Using Multiobjective Evolutionary Algorithm." Translational Vision Science & Technology Jun. 2019, vol. 8, 64.

Juanita N. C., et al., "Improving The Prediction Of Effective Lens Position for Intraocular Lens Power Calculations." Asian J Ophthalmol. 2020;17:233-242.

Norrby S., "Sources of error in intraocular lens power calculation." J Cataract Refract Surg. 2008;34(3):368-376.

Shammas HJ, Chan S., "Precision of biometry, keratometry, and refractive measurements with a partial coherence interferometry-keratometry device." J Cataract Refract Surg. 2010;36(9):1474-1478. doi:10.1016/j.jcrs.2010.02.027.

Cooke DL, Cooke TL, "Comparison of 9 intraocular lens power calculation formulas." J Cataract Refract Surg.2016;42(8):1157-1164. doi:10.1016/j.jcrs.2016.06.029.

Kane JX, et al., "Accuracy of 3 new methods for intraocular lens power selection." JCataract Refract Surg. Published online 2017, 43:333-339, doi:10.1016/j.jcrs.2016.12.021.

Koeppl C, Findl O, Kriechbaum K, et al. "Postoperative change in effective lens position of a 3-piece acrylicintraocular lens." J Cataract Refract Surg. 2003;29(10):1974-1979. doi:10.1016/S0886-3350(02)02049-7.

* cited by examiner $$fELP = \frac{rELP}{LT}$$

METHODS AND SYSTEMS FOR PREDICTING THE POST-OPERATIVE EFFECTIVE LENS POSITION IN CATARACT SURGERY

RELATED APPLICATION

This application claims priority to U.S. Provisional Patent Application No. 63/212,559 entitled Methods and Systems for Predicting the Post-Operative Effective Lens Position in Cataract Surgery, filed Jun. 18, 2021, the entire disclosure of which is expressly incorporated herein by reference.

FIELD

The present disclosure pertains generally to the fields of biomedical engineering and surgery and more particularly to methods and systems for predicting the post-operative effective lens position (ELP) in cataract surgery using a novel pre-operative measurement of the natural lens curvatures.

BACKGROUND

Pursuant to 37 CFR 1.71(e), this patent document contains material that is subject to copyright protection and the owner of this patent document reserves all copyright rights whatsoever.

Cataract surgery is a commonly performed procedure that involves the removal of the crystalline lens and insertion of a synthetic intraocular lens (IOL). The appropriate IOL power in diopters is selected based on the measurements of the patient's eye with ocular biometry measurement devices, and there are many equations that are currently employed for this use. With the improved accuracy of ocular biometry devices, the current greatest limiting factor in predicting postoperative outcomes is effective lens position (ELP), a term used to reference the final resting axial position of the lens, as measured from the front portion of the cornea. It has been estimated that inadequate prediction of effective lens position (ELP) may account for up to 37% of postoperative spherical error. Norrby S., *Sources of error in intraocular lens power calculation*. J Cataract Refract Surg. 2008; 34(3):368-376. doi:10.1016/j.jcrs.2007.10.031.

To predict the ELP, a number of formulas have used. Some of these formulas, such as those known as the Haigis, Holladay and Olsen formulas, have used preoperative anterior chamber depth (ACD) in combination with axial length (AL) to determine the post-operative ELP. see, Olsen T, Olesen H, Thim K, Corydon L. *Prediction of pseudophakic anterior chamber depth with the newer IOL calculation formulas*. J Cataract Refract Surg. 1992; 18(3):280-285. doi:10.1016/50886-3350(13)80905-4; Olsen T, Corydon L, Gimbel H., *Intraocular lens power calculation with an improved anterior chamber depth prediction algorithm*. J Cataract Refract Surg. 1995; 21(3):313-319. doi: 10.1016/S0886-3350(13)80140-X; Olsen T., *Prediction of the effective postoperative (intraocular lens) anterior chamber depth*. J Cataract Refract Surg. 2006; 32(3):419-424. doi: 10.1016/j.jcrs.2005.12.139; and Holladay J T, Prager T C, Chandler T Y, Musgrove K H, Lewis J W, Ruiz R S., *A three-part system for refining intraocular lens power calculations*. J Cataract Refract Surg. 1988 January; 14(1):17-24. doi: 10.1016/s0886-3350(88)80059-2. PMID: 3339543. Others, such as those known as the Barrett, Hoffer Q, and SRK/T formulas, base this calculation more heavily on the AL. Hoffer K J. *The Hoffer Q formula: A comparison of theoretic and regression formulas*. J Cataract Refract Surg.

1993; 19(6):700-712. doi:10.1016/S0886-3350(13)80338-0; and Retzlaff J A, Sanders D R, Kraff M C., *Development of the SRK/T intraocular lens implant power calculation formula*. J Cataract Refract Surg. 1990; 16(3):333-340. doi: 10.1016/S0886-3350(13)80705-5.

Comparisons in postoperative refraction of the various formulas have shown high accuracy of the Olsen formula, especially when optical low coherence tomography (OLCR) is used (Lenstar LS 900, Haag-Streit AG), and high accuracy of the Barrett Universal II when partial coherence tomography (PCI) is used (IOL Master™ 500, Carl Zeiss, Oberkochen, Germany). The Hill-RBF, on the other hand, uses a computerized pattern recognition model to calculate lens power.

In recent years, there have been efforts to improve the accuracy of traditional ELP prediction formulas. For example, a multi-objective evolutionary algorithm (MOEA) which uses multiple parameters has been reported to more accurately predict ELP than the SRK/T and Haigis formulas. The multiple parameters used in this MOEA included: age, gender, preoperative axial length, crystalline lens thickness, central corneal thickness, aqueous depth, anterior surface of the crystalline lens from the posterior cornea) (FIG. 1A), anterior corneal curvature, posterior corneal curvature, angle-to-angle width, angle-to-angle depth, and distance from the posterior cornea to the angle-to-angle line. Tamaoki, A., et al., *Prediction of Effective Lens Position Using Multiobjective Evolutionary Algorithm*, Translational Vision Science & Technology June 2019, Vol. 8, 64. doi: https://doi.org/10.1167/tvst.8.3.64.

Others have reported that the accuracy of ELP prediction may be improved by using ACD+½LT (lens thickness) rather than ACD alone. Juanita, N. C., et al., *Improving The Prediction Of Effective Lens Position for Intraocular Lens Power Calculations*, Asian J Ophthalmol. 2020; 17:233-242; doi 10.35119/ASJOO.V17I2.585.

U.S. Pat. No. 9,554,697 (Padrick et al.), the entire disclosure of which is incorporated herein by reference, describes a method for estimating ELP using the aphakic ocular power of the patient's eye without requiring measurement of the corneal curvature or axial length of the patient's eye.

SUMMARY

Disclosed herein are methods and systems for predicting the post-operative effective lens position (ELP) in cataract surgery using novel pre-operative measurement(s) of the natural lens curvatures.

In accordance with one aspect of the present disclosure, there is provided a method for estimating effective lens position (ELP) of an intraocular lens (IOL) prior to implantation of said IOL in a phakic eye having a native lens, wherein the method uses at least one measurement of a curvature of the native lens of the eye prior to removal of said native lens. In some embodiments, said at least one measurement indicative of a curvature of the native lens may comprises a measurement of an anterior lens surface curvature and a measurement of a posterior lens surface curvature. In some embodiments, the method may further comprise using the measurement of anterior lens surface curvature and the measurement of posterior lens surface curvature to calculate a lens meridian position (LMP). In some embodiments, lens meridian position (LMP) may be the sum of anterior chamber depth (ACD) and the portion of the lens thickness (LT) that lies anterior to the lens meridian position (LMP). In some embodiments, a relative lens meridian position (rLMP) is calculated by subtracting anterior chamber depth (ACD) from the lens meridian position (LMP). In some embodiments, a relative effective lens position (rELP) is calculated by subtracting the anterior chamber depth (ACD) from the effective lens position (ELP). In some embodiments, a fractional lens meridian position (fLMP) is determined by dividing the relative lens meridian position (rLMP) by the lens thickness (LT). In some embodiments, fractional effective lens position (fELP) is then calculated by dividing the relative lens meridian position (rELP) by the pre-operative lens thickness (LT). In some embodiments, any, some or all of lens meridian position (LMP) and/or relative effective lens position (rELP) and/or fractional effective lens position (fELP) is/are may be used as a basis for prediction of, or as an indicator of, post-operative ELP of the IOL. In some embodiments, a curvature of the native lens of the eye may be determined from an optical coherence tomography (OCT) image. In some embodiments, an intraocular lens (IOL) of a particular power may be selected for use in a subject based on the determined relative effective lens position (rELP) and/or fractional effective lens position (fELP).

Further in accordance with the present disclosure, there is provided a method which comprises: a) removing a native lens from an eye of a human or non-human animal subject, b) selecting an intraocular lens (IOL) of a particular power may be selected for use in a subject based on the determined rELP and/or fELP, and c) implanting the selected IOL in the subject's eye from which the native lens was removed. In some applications, this method may be used to replace a cataract or otherwise defective native lens.

Still further in accordance with the present disclosure, there is provided a method for predicting post-operative effective lens position (ELP) of an intraocular lens (IOL) prior to implantation of the IOL, said method comprising the steps of a) obtaining a pre-operative image of a phakic eye having a native lens, b) determining, from the pre-operative image, an anterior chamber depth (ACD); c) determining, from the pre-operative image, a lens meridian position (LMP) by calculating a peripheral intersection of anterior and posterior lens surface curvatures within a central portion of the native crystalline lens; and d) using the LMP to predict the post-operative effective lens position (ELP) of the IOL after implantation. In some embodiments, the step of obtaining a pre-operative image of a phakic eye having a native lens comprises obtaining an anterior segment optical coherence tomography (OCT) image of the central lens surfaces. In some embodiments, the step of using the LMP to predict the post-operative effective lens position (ELP) of the IOL after implantation comprises determining relative effective lens position (rELP) by subtracting the pre-operative anterior chamber depth (ACD) from the effective lens position (ELP). In some embodiments, the step of using the LMP to predict the post-operative effective lens position (ELP) of the IOL after implantation comprises determining a fractional lens meridian position (fLMP) by dividing the rLMP by the thickness of the native crystalline lens (LT). In some embodiments, rELP and/or fELP is/are also or alternatively used as the predicted post-operative ELP of the IOL.

Still further in accordance with the present disclosure, there is provided a method, which may be used to replace a cataract or otherwise diseased or defective lens of a subject's eye, such method comprising: (a) removing a native lens from an eye of a human or non-human animal subject; (b) determining rELP and/or fELP (c) selecting an intraocular lens (IOL) of a particular power for implantation in the eye based on the determined rELP and/or fELP; and (d) implanting the selected IOL in the subject's eye from which the native lens was removed.

Still further in accordance with the present disclosure, there is provided a method for estimating effective lens position (ELP) of an intraocular lens (IOL) prior to implantation of said IOL in a phakic eye having a native lens, said method comprising: (a) determining anterior chamber depth (ACD), thickness of the native lens (LT), and the anterior and posterior surface curvatures of the native lens; (b) calculating relative and fractional lens meridian positions (rLMP and fLMP); and (c) calculating approximate fractional effective lens position (fELP) and in turn the approximate effective lens position (ELP) using a regression model.

Still further in accordance with the present disclosure there is provided a system useable for performing some or all of the methods disclosed herein, said system comprising (a) a biometric apparatus(s) for determining anterior chamber depth (ACD), thickness of the native lens (LT), and the anterior and posterior surface curvatures of the native lens; and a processor or computing apparatus programmed to use the anterior chamber depth (ACD), thickness of the native lens (LT), and the anterior and posterior surface curvatures of the native lens determined by the biometric apparatus(s) to calculate one or more of; relative lens meridian positions (rLMP), fractional lens meridian position (fLMP), approximate fractional effective lens position (fELP) and/or approximate effective lens position (ELP).

Still further in accordance with the present disclosure, there is provided a method for improving an optical biometric system that comprises an apparatus for obtaining measurements of the anterior chamber and/or lens of a subject's eye and a processor or computing apparatus that performs calculations using said measurements, said method comprising: causing the processor or computing apparatus to calculate any, some or all of; to calculate said relative and fractional lens meridian positions (rLMP and fLMP), approximate fractional effective lens position (fELP), and approximate effective lens position (ELP). In some embodiments, this method may be carried out by reprogramming or modifying an existing program of the processor or computing apparatus.

Still further aspects and details of the present disclosure will be understood upon reading of the detailed description and examples set forth herebelow.

BRIEF DESCRIPTION OF THE DRAWINGS

The following figures are included in this patent application and referenced in the following Detailed Description. These figures are intended only to illustrate certain aspects or embodiments of the present disclosure and do not limit the scope of the present disclosure in any way:

FIG. 7A is a graphic showing fELP vs. Aqueous Chamber Depth as measured using the IOL Master™ optical biometer.

DETAILED DESCRIPTION

The following written description and the accompanying figures are intended to describe and illustrate some, but not necessarily all, examples or embodiments of the present disclosure. The described examples or embodiments are to be considered in all respects as illustrative but not restrictive. The contents of this description and the accompanying figures do not limit the scope of this disclosure in any way.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, the articles "a" and "an" are used herein to refer to one or to more than one (i.e., to at least one) of the grammatical object of the article. By way of example, "an element" means one element or more than one element.

The present disclosure includes a new method that uses the anterior and posterior curvatures of the native crystalline lens of the eye to estimate the ELP after cataract surgery. In some embodiments, this method may comprises the steps of:

Measuring the anterior chamber depth (ACD), lens thickness (LT), and the anterior and posterior lens curvatures;

Calculating the relative and fractional lens meridian positions (rLMP and fLMP) as described in our methods; and Calculating an approximate fractional effective lens position (fELP) and in turn the approximate effective lens position (ELP) using a suitable regression model (an example of one such regression model being described below).

Figure 1:
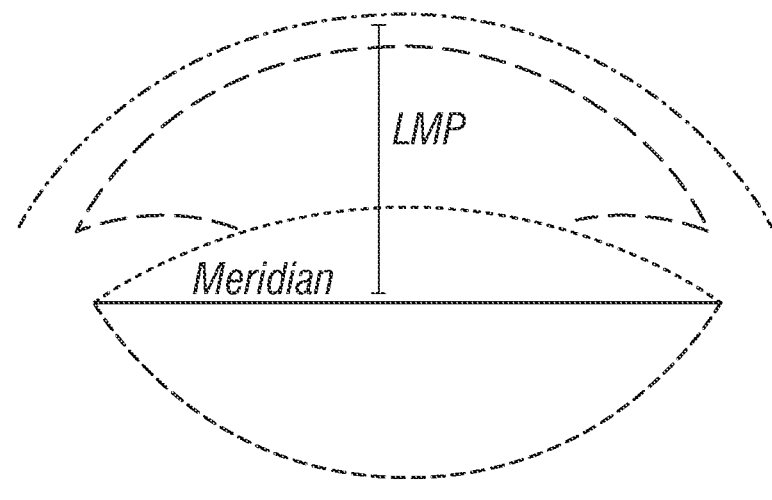
FIG. 1 is a schematic diagram showing lens meridian position (LMP) as determined in accordance with the present disclosure.

In this method, the position of the peripheral lens equator is approximated using anterior segment optical coherence tomography (OCT) images of the central lens surfaces generated during femtosecond laser-assisted cataract surgery (FLACS). FLACS systems use spectral-domain anterior segment OCT scans to target the anterior capsule during capsulorhexis and to avoid the posterior capsule during lens fragmentation. During the image analysis process, the Catalys® Precision Laser System (Johnson & Johnson Vision, Santa Ana, CA) calculates a parameter called the lens meridian position (LMP). The LMP is a theoretical parameter generated by calculating the peripheral intersection of the anterior and posterior lens surface curvatures as measured within the central visible portion of the lens (see FIG. 1 below). The lens meridian position (LMP) is a theoretical parameter which can be generated by the Catalys® System by calculating the theoretical peripheral intersection of the anterior and posterior lens surface curvatures as measured within the central visible portion of the lens (FIG. 1). As shown schematically in FIG. 1, lens meridian position (LMP) measurements were extracted from pre-operative OCT image sets generated by the Catalys® Precision Laser System.

Figure 2:
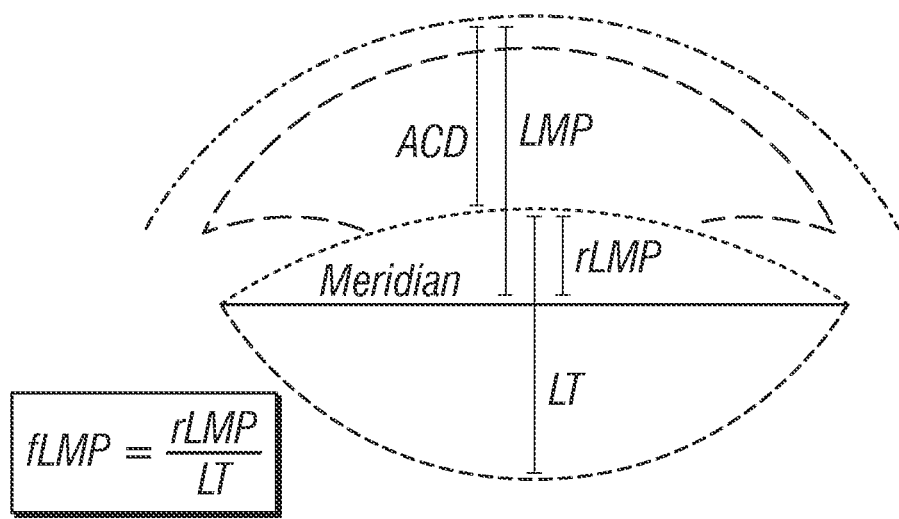
FIG. 2 is a schematic diagram showing fLMP represents a description of the position of the theoretical lens meridian in a manner that is independent of both the size and location of the lens.

In its raw form, the LMP is essentially the sum of two anatomic components: the ACD, and the portion of the LT that lies anterior to the theoretical lens meridian. The ACD and LT are both established parameters with known biometric significance, so in order to identify any novel biometric significance of the LMP, it was necessary to first factor out the ACD and LT. To this end, two new terms were defined. The relative lens meridian position (rLMP) is calculated by subtracting the ACD from the LMP, and thus represents the axial position of the lens meridian relative to the ACD, but in a manner independent of the ACD itself. The fractional lens meridian position (fLMP) is then calculated by dividing the rLMP by the LT, and thus represents the fraction of the LT that lies anterior to the lens meridian, but in a manner independent of the LT itself. As such, the fLMP represents a description of the position of the theoretical lens meridian in a manner that is independent of both the size and location of the lens, as shown in the diagram of FIG. 2.

Figure 3:
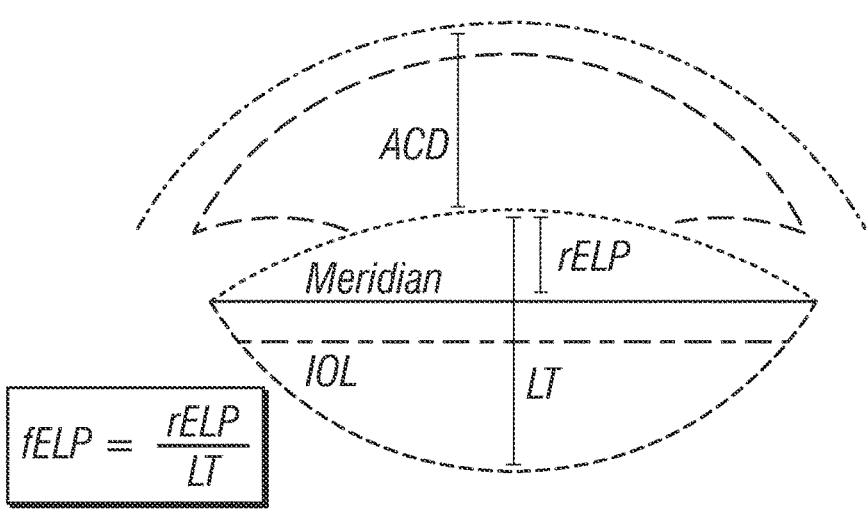
FIG. 3 is a schematic diagram showing that rfELP describes the post-operative position of the IOL within the extents of the pre-operative capsular bag in a manner that is independent of both the size and location of the pre-operative capsular bag.

In its raw form, the ELP is also essentially the sum of two anatomic components: the pre-operative ACD, and the relative deepening of the ACD that occurs as a result of replacing the natural lens with an IOL. In order to identify anatomic parameters with a capacity to predict the ELP, the current invention factors the ACD and LT out of the ELP. This was necessary to ensure that any statistical association between the ELP and a candidate predictive variable was not simply an artifact of a correlation between the candidate predictive variable and the ACD or LT. To this end, two additional new terms were defined. The relative effective lens position (rELP) is calculated by subtracting the pre-operative ACD from the ELP, and thus represents the axial position of the IOL relative to the pre-operative ACD, but in a manner independent of the pre-operative ACD itself. The fractional effective lens position (fELP) is then calculated by dividing the rELP by the pre-operative LT, and thus represents the post-operative deepening of the ACD as a fraction of the pre-operative LT, but in a manner independent of both the ACD and the LT themselves. As such, the fELP describes the post-operative position of the IOL within the extents of the pre-operative capsular bag in a manner that is independent of both the size and location of the pre-operative capsular bag, as shown in the diagram of FIG. 3.

Characterization of the fLMP

Figure 4:
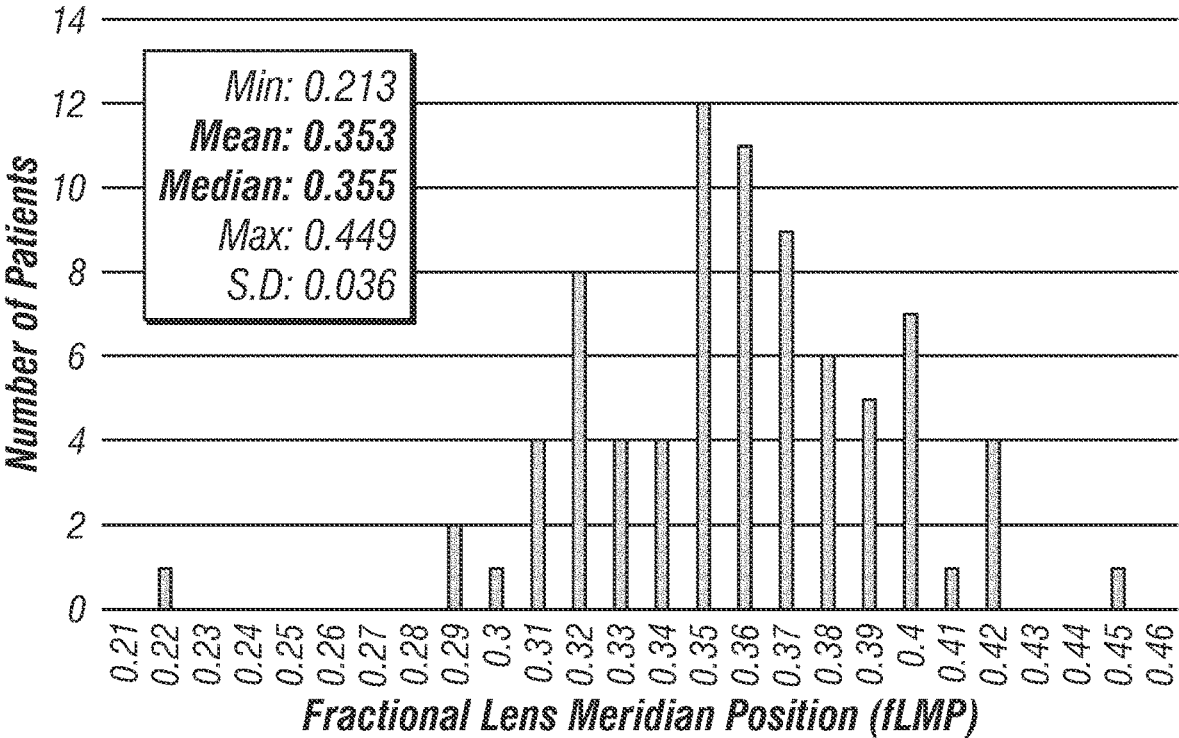
FIG. 4 is a graphic (with statistics) showing the fLMP population distribution in human test subjects.

In this study, fLMP followed an approximately normal distribution, with the lens meridian sitting behind the anterior lens surface by an average of ~35% of the total lens thickness. This is shown in graphic form in FIG. 4, below.

Figure 5A:
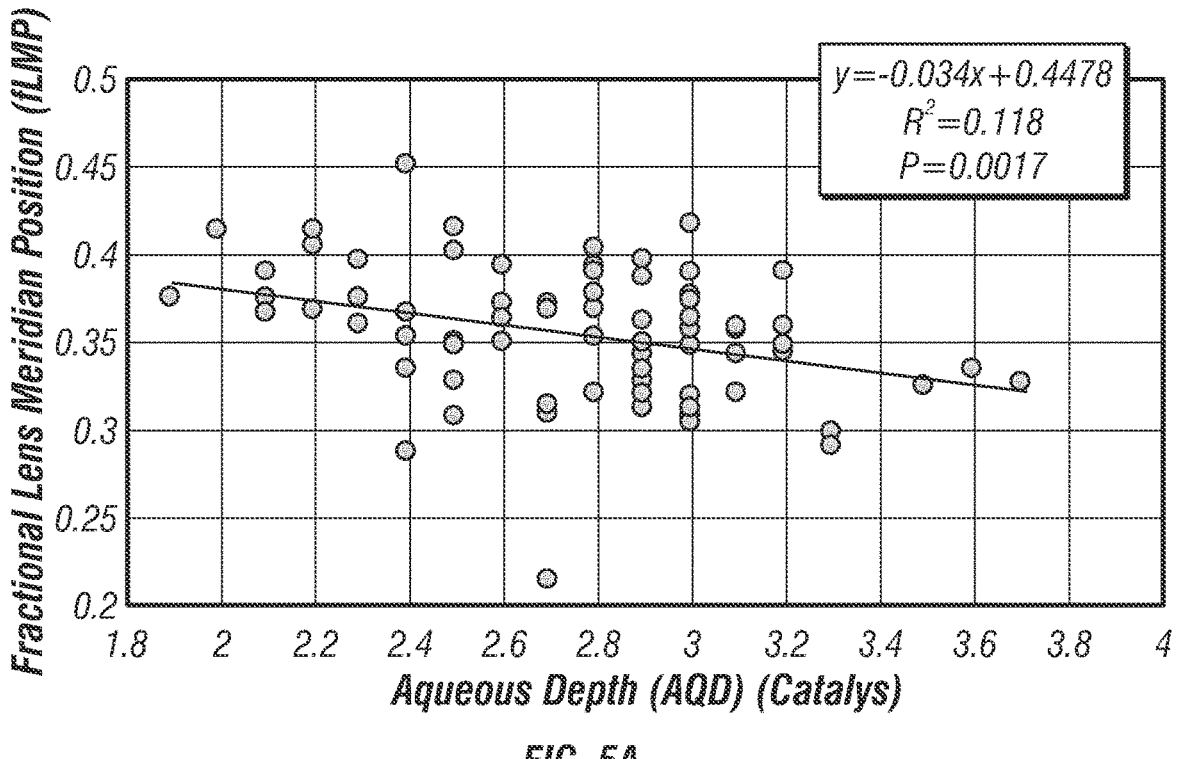
FIG. 5A is a graphic showing fLMP vs. AQD in human subjects, as measured using the Catalys® Precision Laser System.
Figure 5B:
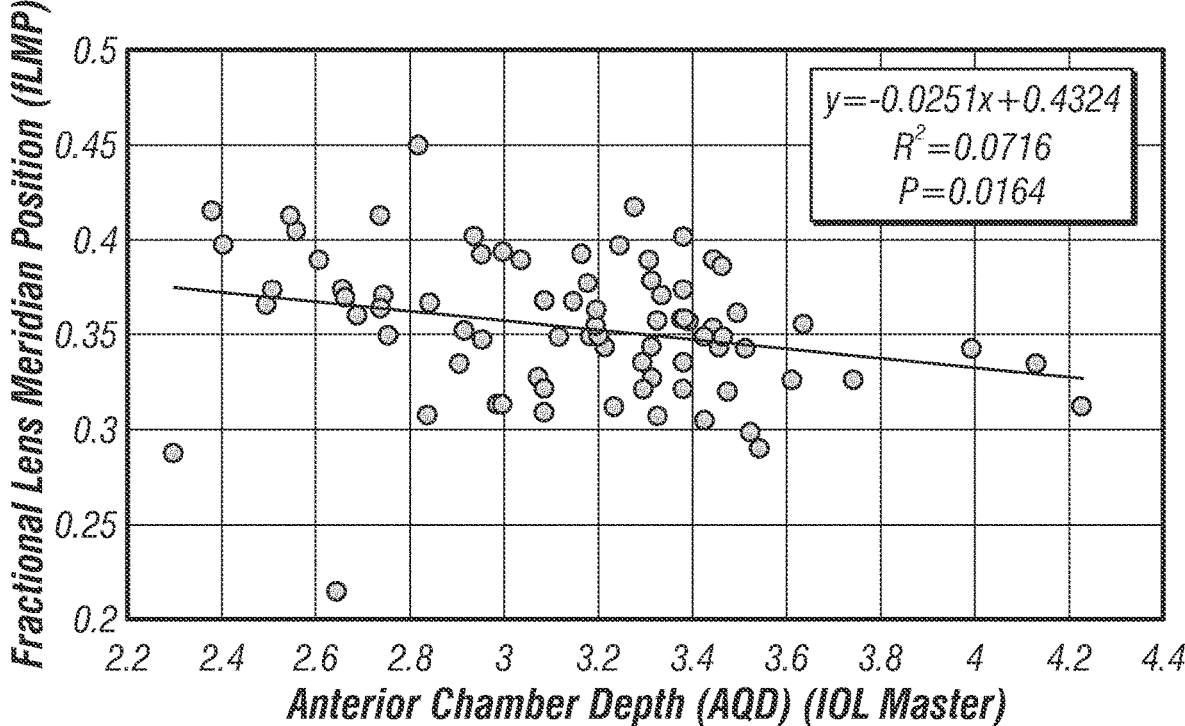
FIG. 5B is a graphic showing fLMP vs. AQD in human subjects, as measured using the IOL Master™ optical biometer.
Figure 5C:
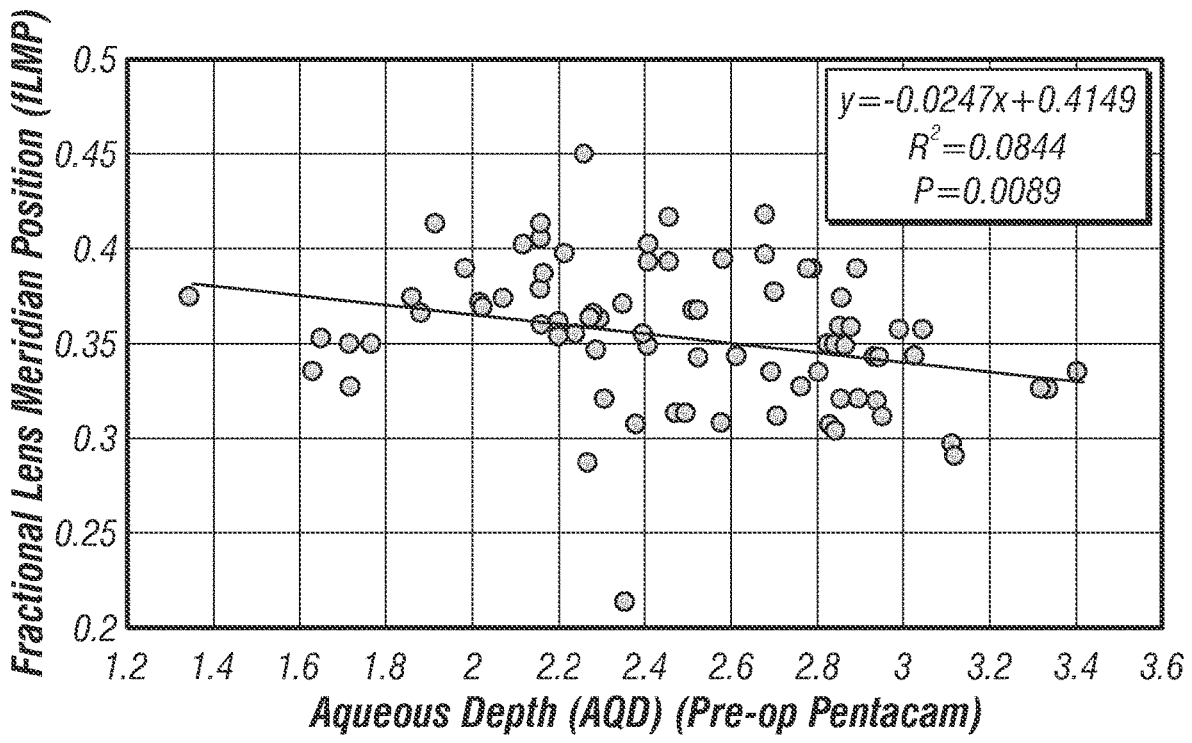
FIG. 5C is a graphic showing fLMP vs. AQD in human subjects, as measured using the Pentacam™ camera system.

This disclosure explains how the fLMP contains novel anatomic information, and has been analyzed by a multivariate regression model of the fLMP using traditional biometric parameters as independent variables. To avoid statistical confusion between analogous variables, the biometry data was obtained using each of three devices, namely the above-referenced Catalys® Precision Laser System (FIG. 5A), the IOL Master™ Optical Biometer (FIG. 5B) and the Pentacam™ Camera System (Oculus Optikgeräte GmbH) (FIG. 5C) and such data were analyzed separately. In each of the three regression models, the only pre-operative biometric parameter that was statistically associated with the fLMP was the ACD, with narrower chambers being associated with more posterior lens meridians. Subsequent univariate regression analyses confirmed that this relationship was highly statistically significant in each case, as shown graphically in FIGS. 5A, 5B and 5C, below, with the statistically-significant relationship between fLMP and ACD persisting even when age is included as an independent variable.

Characterization of the fELP

Figure 6:
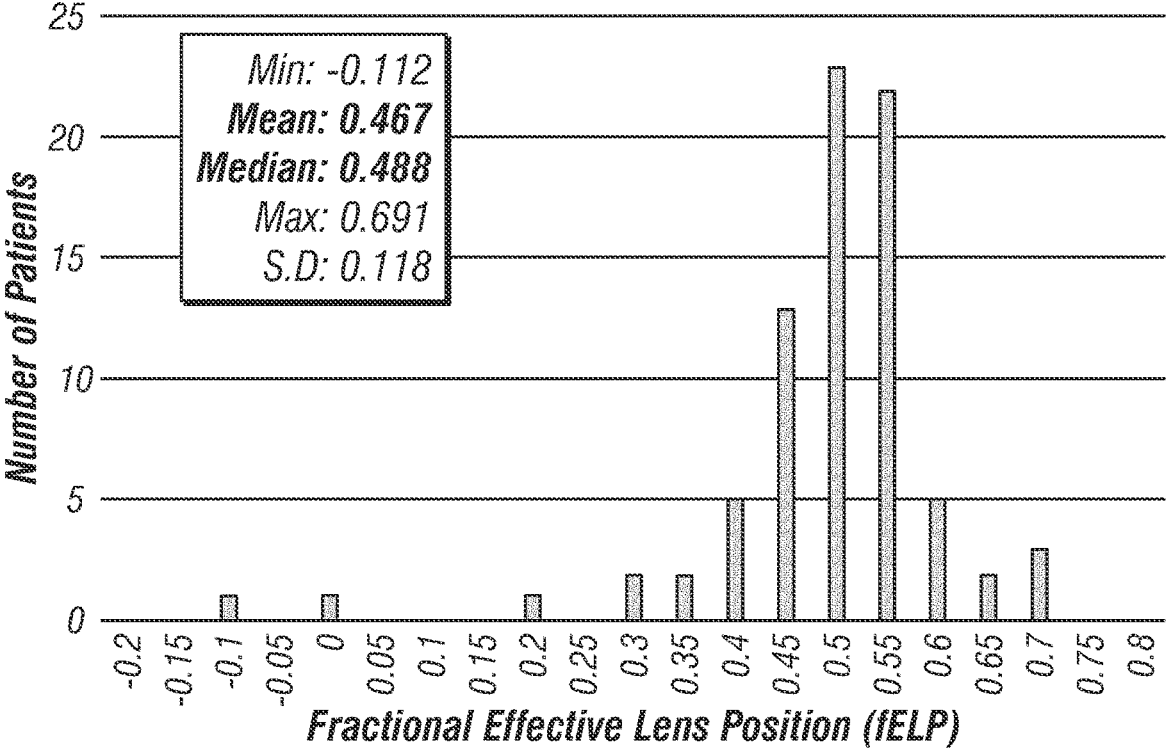
FIG. 6 is a graphic (with statistics) showing an fELP distribution in human test subjects which follows an approximately normal distribution, with the IOL coming to rest behind the anterior lens surface by an average of ~47% of the total pre-operative lens thickness (mean 0.467, S.D. 0.118).

As shown in FIG. 6, the fELP follows an approximately normal distribution, with the IOL coming to rest behind the anterior lens surface by an average of ~47% of the total pre-operative lens thickness (mean 0.467, S.D. 0.118).

Figure 7A:
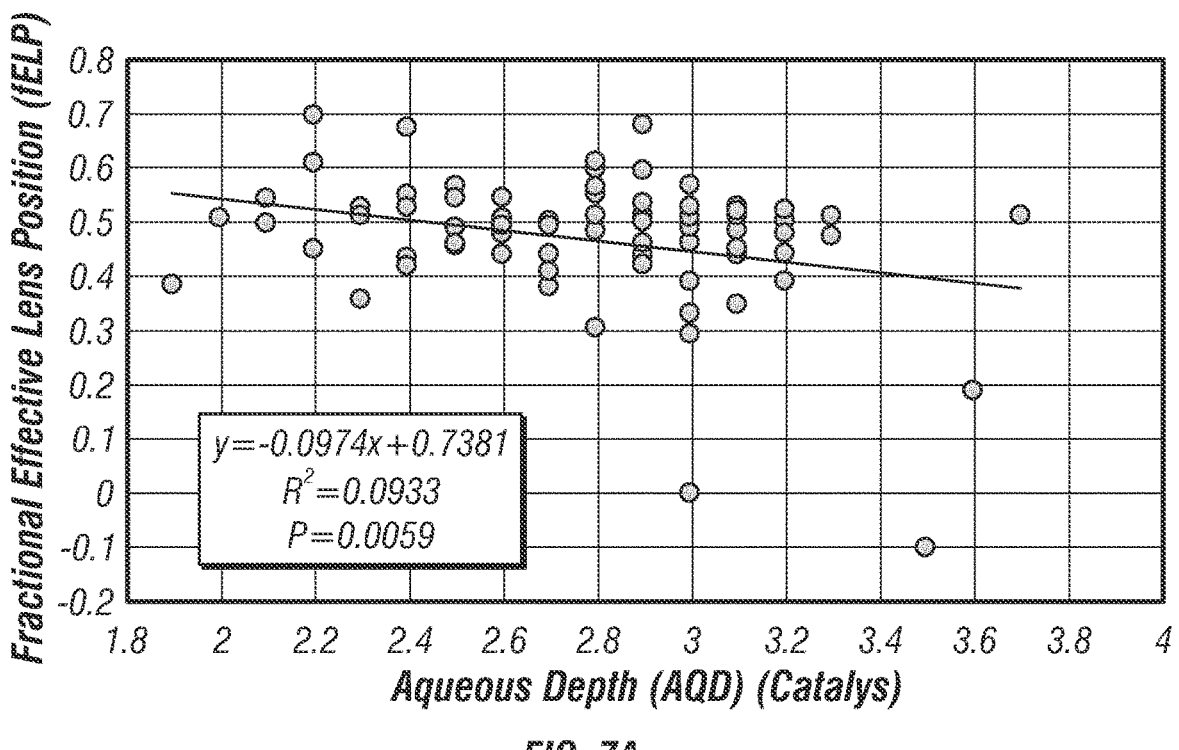
FIG. 7A is a graphic showing fELP vs. Aqueous Chamber Depth as measured using the Catalys® Precision Laser System.
Figure 7B:
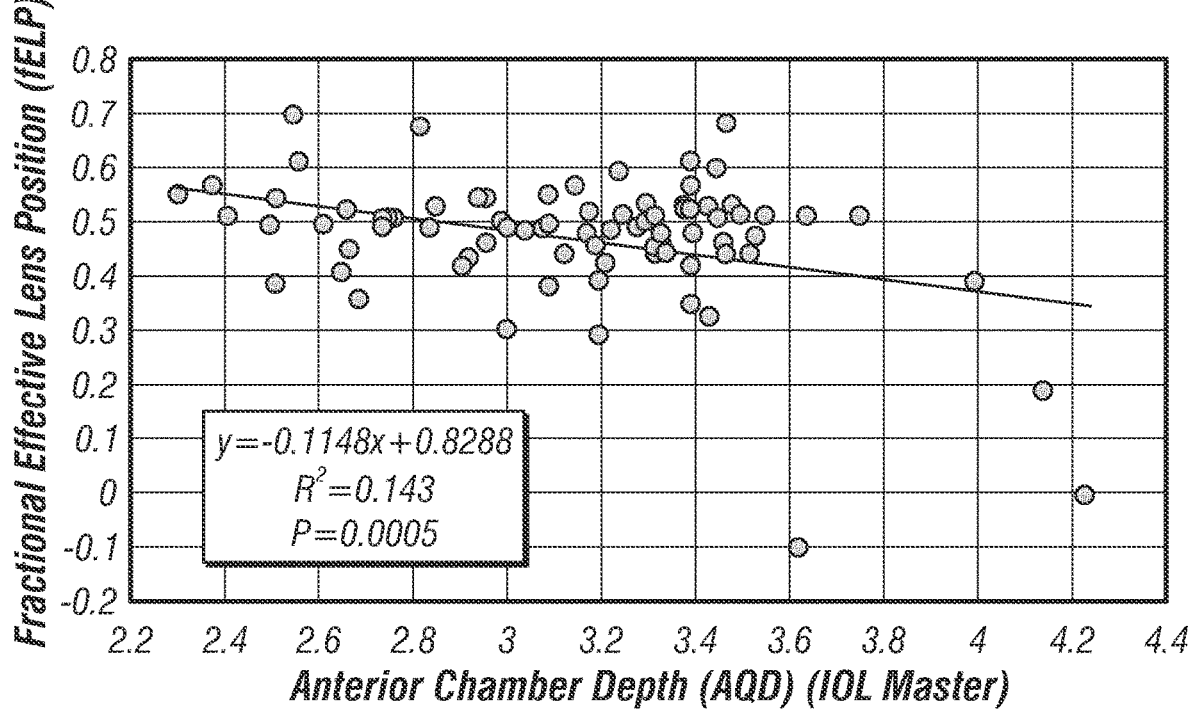
FIG. 7C is a graphic showing fELP vs. Aqueous Chamber Depth as measured using the Pentacam™ camera system.
Figure 7C:
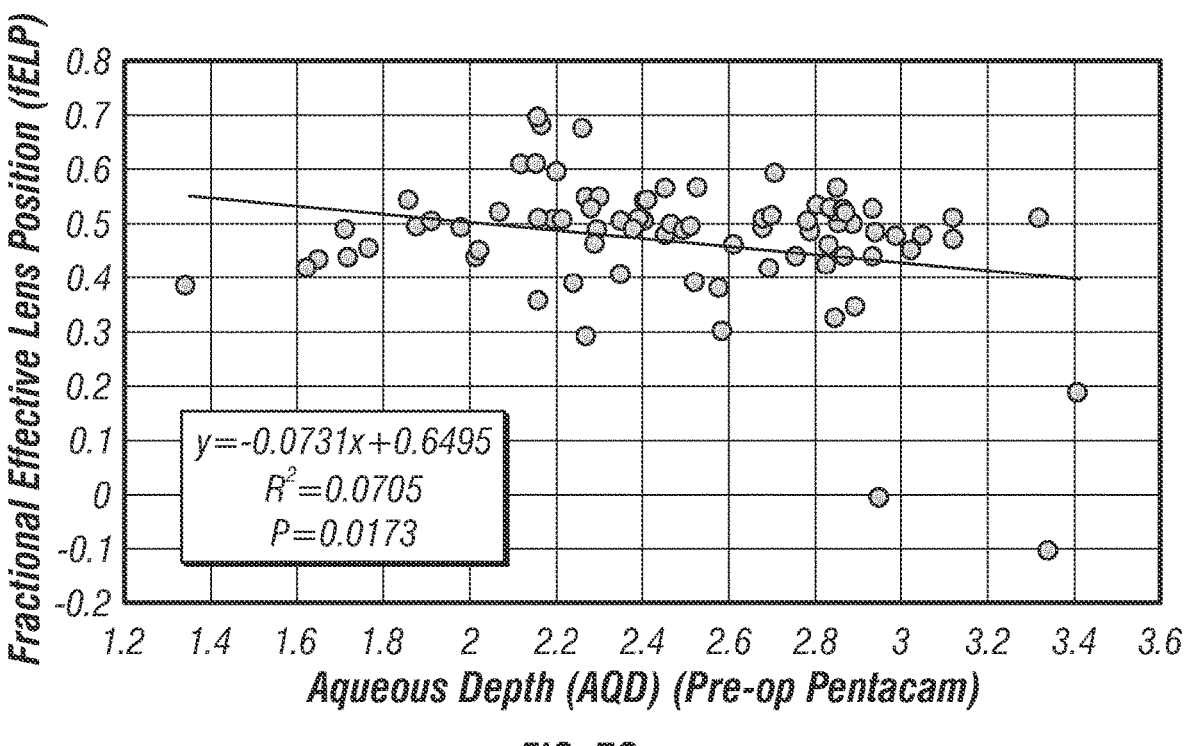

In order to examine the extent to which the fELP was related to standard pre-operative biometric parameters, a multivariate regression model of the fELP was generated using the other biometric parameters as independent variables. As with the fLMP analyses, the biometry data from the Catalys, IOL master, and Pentacam machines were analyzed separately to avoid statistical confusion between similar variables. Similar to results from the fLMP analyses, the only standard pre-operative biometric parameter that was statistically associated with the fELP was the ACD, with narrower pre-operative chambers being associated with more posterior post-operative IOL positions. Subsequent univariate regression analyses confirms that this relationship is highly statistically significant in each case. FIGS. 7A, 7B and 7C are graphs showing the relationship between the fELP and the ACD, as measured by each of three modalities. The R2 and p-values shown represent the results of univariate regression analyses.

Relationship Between the fLMP and the fELP

Figure 8:
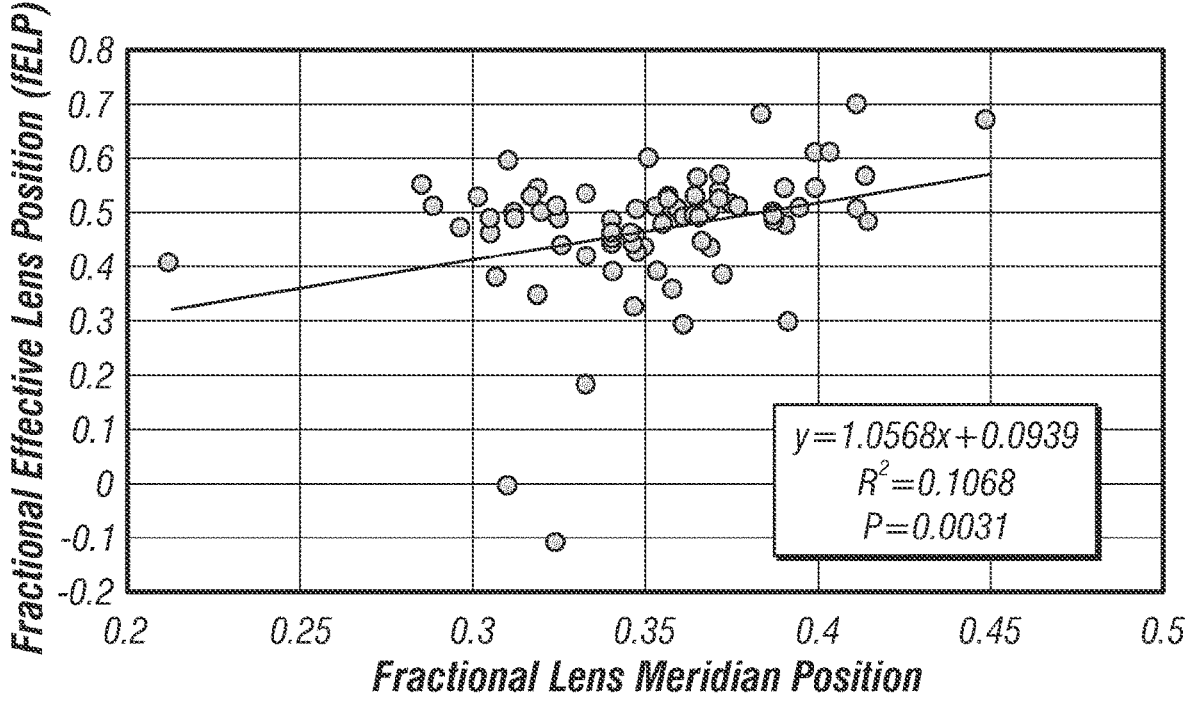
FIG. 8 is a graphic showing fELP vs. Functional Lens Meridian Position (with statistics) showing a significant positive correlation between those variables.

In order to examine the extent to which the fLMP might inform predictions of the fELP, and in turn the ELP itself, a univariate regression model of the fELP was generated using the fLMP as the independent variable. This model confirmed a strong positive correlation between the two variables, with a nearly 1:1 slope and a high degree of statistical significance (FIG. 8).

We determined whether the positive correlation observed between the fLMP and fELP was merely an artifact of their mutual negative correlations to the ACD. To test this hypothesis, a multivariate regression analysis was performed using both the fLMP and ACD as independent variables attempting to predict the fELP. This analysis was performed in triplicate, once for each of the three ACD measurement systems. In all three cases, the positive correlation between the fELP and the fLMP maintained its statistical significance, confirming that the relationship is independent of any mutual correlation to the ACD.

ELP Modelling

Next, a series of six linear regression models were constructed to compare the ELP-predictive capacity of various combinations of pre-operative variables. The models were constructed to predict the rELP, which can then be added to the pre-operative ACD to give a prediction of the full ELP. Factoring the ACD out of the dependent variable in this manner allowed the models to examine the extent to which the relative deepening of the ACD (rELP) depends on the ACD itself. The independent variables for each model were a combination of the ACD, LT, and rLMP. The relative LMP and ELP variables were used because they are expressed in the same distance units as the other variables, whereas the fLMP and fELP are unitless fractions. To control for inter-device variability, both pre-operative ACD and post-operative ACD measurements were taken from Pentacam scans. Lens thickness and lens meridian measurements were taken from Catalys scans. To account for differing numbers of independent variables, the models were compared by examining adjusted R2 values as summarized in Table 1, below.

TABLE 1

Table 1: rELP model results. Model equations include the regression-optimized coefficients for each variable. Adjusted R2 values show the extent to which variability in the rELP can be predicted by each model.

| | Equation | Adjusted $R^2$ |
|---|---|---|
| Model 1 | rELP = 3.52 + (−0.53 * ACD) | 0.151 |
| Model 2 | rELP = 1.32 + (−0.35 * ACD) + (0.37 * LT) | 0.208 |
| Model 3 | rELP = 0.34 + (1.12 * rLMP) | 0.255 |
| Model 4 | rELP = 0.20 + (1.05 * rLMP) + (0.05 * LT) | 0.246 |
| Model 5 | rELP = 1.37 + (−0.27 * ACD) + (0.91 * rLMP) | 0.279 |
| Model 6 | rELP = 1.43 + (−0.28 * ACD) + (0.93 * rLMP) + (−0.01 * LT) | 0.270 |

When ACD was used as the only independent variable, regression modelling accounted for only about 15% of rELP variability (model 1, R2=0.151), but addition of the LT improved this prediction to about 21% (model 2, R2=0.208).

In comparison, when rLMP was used as the only independent variable, regression modelling accounted for almost 26% of rELP variability (model 3, R2=0.255), and addition of the LT offered no additional improvement (model 4, R2=0.246).

Use of both ACD and rLMP as independent variables, provided only about a 2% improvement over rLMP alone (model 5, R2=0.279), and addition of the LT again offered no additional improvement (model 6, R2=0.270).

These results indicate that models based on the LMP are substantially better at predicting the ELP than are models based on the ACD. However, it is important to note that the best ELP predictions were generated when the ACD and fLMP were both taken into account, indicating that measurements of the LMP might best serve to augment rather than replace current IOL power-prediction methods.

Accordingly, the method disclosed herein provide an improvement over current methods for approximating the ELP. This improvement in ELP approximation will allow physicians to improve the accuracy of their IOL calculations and achieve superior refractive outcomes after cataract surgery. Our method for approximating the ELP is superior to prior methods due to employing a novel set of pre-operative measurements and applying a novel mathematical method.

In summary, a method for pre-operative estimation of post-operative ELP of an IOL may comprise following steps:

1. Measurement of the anterior chamber depth (ACD), lens thickness (LT), and the anterior and posterior lens curvatures.

2. Calculation of the relative and fractional lens meridian positions (rLMP and fLMP); and
3. Calculation of an approximate fractional effective lens position (fELP) and in turn the approximate effective lens position (ELP) using either one of the regression models described above or another model (which may be based on a larger study with more eyes).

The methods described herein and apparatus to facilitate their use may be incorporated into the hardware, software or programming of devices, such as biometry devices and biometry components of cataract surgery consoles or systems such that the herein-described methods may be performed by those devices. For example, a system according to this disclosure may comprise biometric apparatus in combination with a processor or computing device, wherein a) the biometric apparatus is configured to determine anterior chamber depth (ACD), thickness of the native lens (LT), and the anterior and posterior surface curvatures of the native lens and b) the processor or computing apparatus is programmed to use the anterior chamber depth (ACD), thickness of the native lens (LT), and the anterior and posterior surface curvatures of the native lens determined by the biometric apparatus to calculate said relative and fractional lens meridian positions (rLMP and fLMP), approximate fractional effective lens position (fELP), and approximate effective lens position (ELP).

Although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for estimating effective lens position (ELP) of an intraocular lens (IOL) prior to implantation of said IOL in a phakic eye having a native lens, said system comprising:
    at least one biometric apparatus for obtaining at least one measurement of a curvature of the native lens of the eye prior to removal of said native lens; and
    a computer or processor programmed to determine with use of said measurement, said estimated effective lens position (ELP);
    wherein said at least one measurement indicative of a curvature of the native lens comprises a measurement of an anterior lens surface curvature and a measurement of a posterior lens surface curvature; and
    wherein the computer or processor is programmed to use the measurement of an anterior lens surface curvature and the measurement of a posterior lens surface curvature to calculate a lens meridian position (LMP) by determining the sum of anterior chamber depth (ACD) and the portion of the lens thickness (LT) that lies anterior to the lens meridian position (LMP).

2. A system according to claim 1 wherein the computer or processor is further programmed to determine relative lens meridian position (rLMP) by subtracting the anterior chamber depth (ACD) from the lens meridian position (LMP).

3. A system according to claim 2 wherein the computer or processor is further programmed to determine relative effective lens position (rELP) by subtracting the anterior chamber depth (ACD) from the estimated effective lens position (ELP).

4. A system according to claim 2 wherein the computer or processor is further programmed to determine fractional lens meridian position (fLMP) by dividing the relative lens meridian position (rLMP) by the lens thickness (LT).

5. A system according to claim 1 wherein said at least one biometric apparatus obtains said measurement of a curvature of the native lens of the eye from an optical coherence tomography (OCT) image.

6. A system for estimating effective lens position (ELP) of an intraocular lens (IOL) prior to implantation of said IOL in a phakic eye having a native lens, said system comprising:
    at least one biometric apparatus for obtaining at least one measurement of a curvature of the native lens of the eye prior to removal of said native lens; and
    a computer or processor programmed to determine with use of said measurement, said estimated effective lens position (ELP);
    wherein the said at least one biometric apparatus is operative to:
        obtain a pre-operative image of a phakic eye having a native lens; and
        determine, from the pre-operative image, an anterior chamber depth (ACD); and
    wherein the computer or processor is programmed to:
        determine, from the pre-operative image, a lens meridian position (LMP) by calculating a peripheral intersection of anterior and posterior lens surface curvatures within a central portion of the native crystalline lens; and
        use the lens meridian position LMP to calculate said estimated effective lens position (ELP).

7. A system according to claim 6 wherein the pre-operative image of a phakic eye having a native lens comprises an anterior segment optical coherence tomography (OCT) image of central lens surfaces.

8. A system according to claim 6 wherein the computer or processor is programmed to calculate relative effective lens position (rELP) by subtracting the pre-operative anterior chamber depth (ACD) from the estimated effective lens position (ELP).

9. A system according to claim 8 wherein the computer or processor is programmed to determine a fractional lens meridian position (fLMP) by dividing the rLMP by the thickness of the native crystalline lens (LT).

10. A system for estimating effective lens position (ELP) of an intraocular lens (IOL) prior to implantation of said IOL in a phakic eye having a native lens, said system comprising:
    at least one biometric apparatus for obtaining at least one measurement of a curvature of the native lens of the eye prior to removal of said native lens; and
    a computer or processor programmed to determine with use of said measurement, said estimated effective lens position (ELP);

wherein said at least one biometric apparatus determines anterior chamber depth (ACD), thickness of the native lens (LT), and the anterior and posterior surface curvatures of the native lens; and wherein the computer or processor is programmed to:
calculate relative and fractional lens meridian positions (rLMP and fLMP);
calculate approximate fractional effective lens position (fELP); and
determine said estimated effective lens position (ELP) using a regression model.

11. A system according to claim 10, wherein:

said at least one biometric apparatus determines said anterior chamber depth (ACD), thickness of the native lens (LT), and anterior and posterior surface curvatures of the native lens; and the computer or processor is programmed to use the anterior chamber depth (ACD), thickness of the native lens (LT), and the anterior and posterior surface curvatures of the native lens determined by said at least one biometric apparatus to calculate said relative and fractional lens meridian positions (rLMP and fLMP), approximate fractional effective lens position (fELP), and approximate effective lens position (ELP).

\* \* \* \* \*